US00PP09324P

United States Patent [19]

Zary

[11] Patent Number: Plant 9,324

[45] Date of Patent: Oct. 17, 1995

[54] SHRUB ROSE PLANT NAMED 'JACLOVER'

[75] Inventor: Keith W. Zary, Thousand Oaks, Calif.

[73] Assignee: Bear Creek Gardens, Inc., Medford, Oreg.

[21] Appl. No.: 335,634

[22] Filed: Nov. 8, 1994

[51] Int. Cl.[6] ..... A01H 5/00

[52] U.S. Cl. ..... Plt./1

[58] Field of Search ..... Plt./1, 7.1, 22, Plt./11

*Primary Examiner*—Howard J. Locker

*Attorney, Agent, or Firm*—Klarquist Sparkman Campbell Leigh & Whinston

[57] ABSTRACT

A shrub rose plant having low spreading habit, unique lavender colored flowers, resistance to powdery mildew and rust, seven leaflet leaves, and ease of production from softwood cuttings.

1 Drawing Sheet

The present invention relates to a new and distinct variety of rose plant of the hybrid tea class which was originated by me by crossing the variety KORimro (unpatented) with the variety JACare, U.S. Plant Pat. No. 6,515.

The primary objective of this breeding was to produce a new rose variety having the low spreading habit and good disease resistance of the female parent combined with the repeat blooming characteristic and larger flowers of JACare. This objective was substantially achieved, along with other desirable improvements, as evidenced by the following unique combination of characteristics that are outstanding in the new variety and that distinguish it from its parents, as well as from all other varieties of which I am aware:

1. Low spreading habit;
2. Unique lavender colored flowers;
3. Resistance to powdery mildew and rust;
4. Seven leaflet leave are normal; and
5. Ease of production from softwood cuttings.

Asexual reproduction of this new variety by budding and softwood cuttings, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with the Royal Horticultural Society (London) Colour Chart, except where ordinary dictionary significance of color is indicated.

Parentage:

*Seed parent.*—KORimro.

*Pollen parent.*—JACare.

Classification:

*Botanical.*—*Rosa hybrida.*

*Commercial.*—Shrub.

FLOWER

Observations made from specimens grown in a garden environment at Somis, Calif., March to July 1994.

Blooming habit: Recurrent.

Bud:

*Size.*—½ inch long when the petals start to unfurl.

*Form.*—The bud form is short, pointed ovoid.

*Color.*—When sepals first divide, bud color is Greyed Purple 186A. When half blown, the upper sides of the petals are Greyed Purple 186D; and the lower sides of the petals are Greyed Purple 186D.

*Sepals.*—Color: Green Group 138C. Surface texture: Covered in fine hairs. There are three lightly appendaged sepals. There are two unappendaged sepals with hairy edges.

*Receptacle.*—Color: Green Group 137D. Shape: Funnel. Size: Small (⅛ inch×¼ inch). Surface: Smooth.

*Peduncle.*—Length: Short (¾ inch to 1 inch). Surface: Glandular. Color: Light green. Strength: Stiff, erect, slender.

Bloom:

*Size.*—Small. Average open size is 1¾ inches to 2 inches).

*Borne.*—Singly or several together in flat clusters.

*Stems.*—Long, Strong. Average length is about 10 inches.

*Form.*—When first open: Flat. Permanence: Retains its form to the end.

*Petalage.*—Number of petals under normal conditions: 10 to 15.

*Color.*—The upper sides of the petals are Greyed Purple 186D. The reverse sides of the petals are Greyed Purple 186D. The base of each petal has a small whitish green half moon at the point of attachment (⅛ inch×⅛ inch). The major color on the upper side is Greyed Purple 186D.

*Variegations.*—White streaks on several petals in a flower.

*Discolorations.*—The general tonality at the end of the first day: No change. At the end of the third day, flowers have shattered.

*Fragrance.*—Slight.

Petals:

*Texture.*—Thin.

*Shape.*—Deltoid.

*Form.*—Flat.

*Arrangement.*—Imbricated, with a few petaloids in the center.

*Persistence.*—Drop off cleanly.

*Lastingness.*—On the plant: Short (2 to 3 days). As a cut flower: Not tested.

Reproductive parts:

*Anthers.*—Size: Medium. Quantity: Many. Color: Yellow. Arrangement: Regular around styles.

*Filaments.*—Color: White.

*Pollen.*—Color: Gold yellow.

*Styles.*—Color: Greenish white.

*Stigmas.*—Color: Greenish white.

Form: Rambler.

Growth: Very vigorous, branching, sprawling; JAClover can best be described as ground cover. At three years, unpruned it is 6 to 8 feet wide and 2 feet tall.

Foliage: Number of leaflets on normal mid-stem leaves: 7.

*Size.*—Small (3½ inches×2 inches).

*Quantity.*—Abundant.

*Color.*—New foliage: Greyed Purple 183D. Old foliage: Green Group 137A on the upper side and Green Group 137C on the lower side.

Leaflets:

*Shape.*—Pointed oval.

*Texture.*—Upper side: Leathery, glossy.

*Edge.*—Serrated.

*Serration.*—Single, small.

*Petiole rachis.*—Color: Green.

*Petiole underside.*—Rough with prickles and glands.

*Stipules.*—Long, serrated, bearded, glandular.

*Disease resistance.*—Resistant to mildew and rust under normal growing conditions at Somis, Calif.

Wood:

*New wood.*—Color: Reddish. Bark: Smooth.

*Old wood.*—Color: Green. Bark: Smooth.

Prickles:

*Quantity.*—On main canes from base: Many. On laterals from main canes: Many.

*Form.*—Medium, hooked downward.

*Color when young.*—Red.

Small prickles:

*Quantity.*—On main stalks: Few. On laterals: None.

*Color.*—Reddish brown.

I claim:

1. A new and distinct variety of rose plant of the shrub class, substantially as herein shown and described, characterized particularly as to novelty by the unique combination of its low spreading habit, unique lavender colored flowers, resistance to powdery mildew and rust, seven leaflet leaves, and ease of production from softwood cuttings.

* * * * *

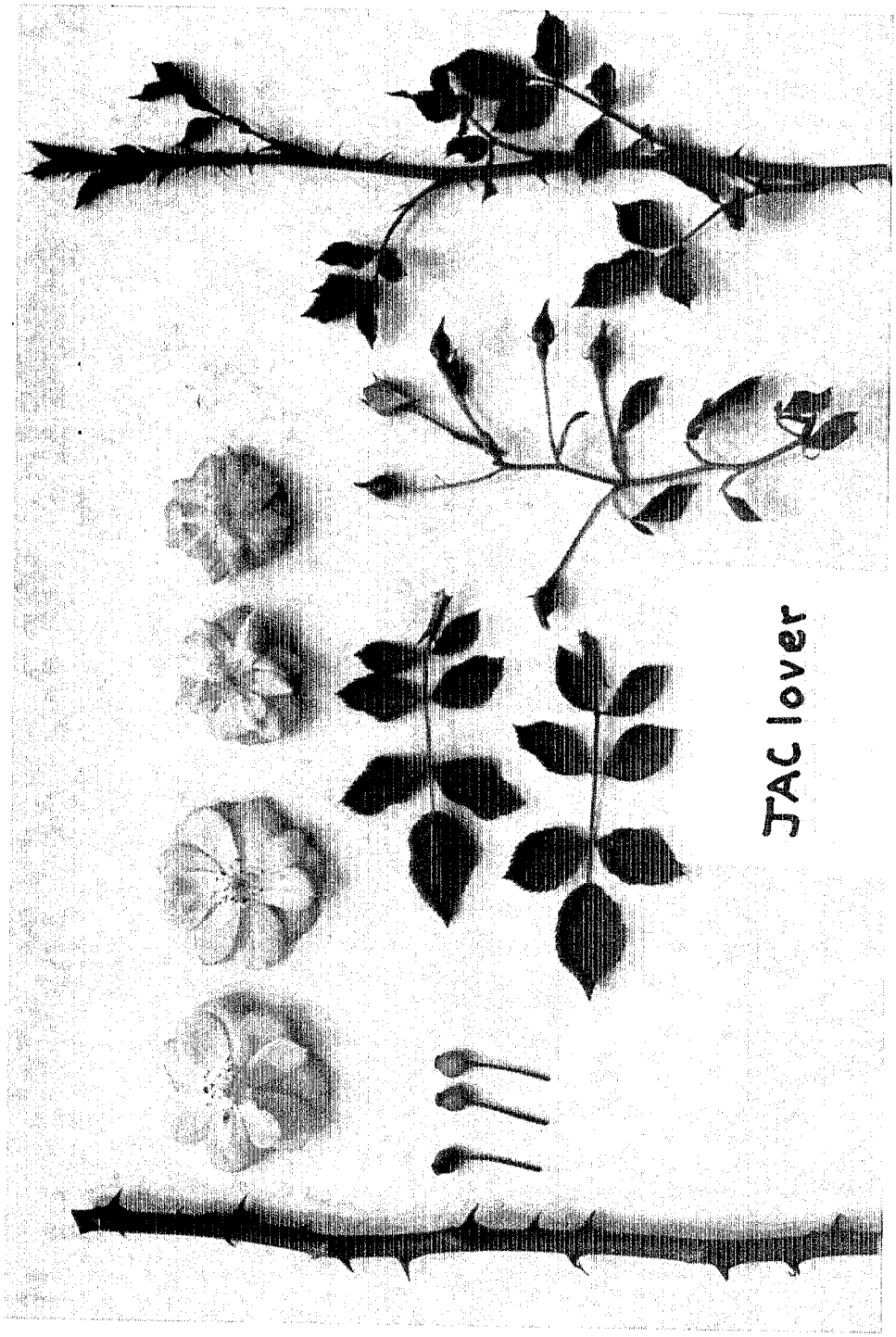
JAC lover